(12) United States Patent
Nat

(10) Patent No.: US 7,059,348 B2
(45) Date of Patent: Jun. 13, 2006

(54) DRUG DELIVERY SYSTEM

(75) Inventor: Avtar S. Nat, Saratoga, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 10/438,282

(22) Filed: May 13, 2003

(65) Prior Publication Data

US 2005/0197652 A1 Sep. 8, 2005

Related U.S. Application Data

(60) Provisional application No. 60/380,784, filed on May 13, 2002.

(51) Int. Cl.
*A61M 7/00* (2006.01)
*F16K 11/20* (2006.01)
*F16K 31/145* (2006.01)

(52) U.S. Cl. .................. 137/597; 251/61.1; 604/891.1

(58) Field of Classification Search ............. 604/891.1; 128/903; 137/597; 251/61.1
See application file for complete search history.

(56) References Cited

U.S. PATENT DOCUMENTS

| | | | | |
|---|---|---|---|---|
| 4,373,527 A | * | 2/1983 | Fischell | 604/891.1 |
| 5,665,070 A | * | 9/1997 | McPhee | 604/131 |
| 6,408,878 B1 | * | 6/2002 | Unger et al. | 137/597 |
| 6,520,936 B1 | * | 2/2003 | Mann | 604/141 |

* cited by examiner

*Primary Examiner*—Nicholas D. Lucchesi
*Assistant Examiner*—Roz Maiorino
(74) *Attorney, Agent, or Firm*—Townsend and Townsend and Crew LLP

(57) ABSTRACT

An implantable drug delivery system has a housing, a collapsible reservoir, a microfabricated flow channel, and at least one magnet. The collapsible reservoir is disposed in the housing. The microfabricated flow channel is connected at one end to the collapsible reservoir and opens at an external surface of the housing. The magnet is disposed within the housing adjacent a membrane defining the flow channel and is movable in response to a magnetic force to deflect the membrane into the flow channel for inhibiting drug flow from the collapsible reservoir to the external surface of the housing, and for pumping drug flow from the collapsible reservoir to the external surface of the housing.

7 Claims, 5 Drawing Sheets

A Implantable Drug Delivery Device

A Transdermal Body Fluids Sampling Device

DRUG DELIVERY SYSTEM

CROSS REFERENCE TO RELATED APPLICATION

This application is a nonprovisional of, and claims the benefit of the filing date of U.S. Provisional Appl. No. 60/380,784, entitled "DRUG DELIVERY SYSTEM," filed May 13, 2002 by Avtar S. Nat, the entire disclosure of which is incorporated herein by reference for all purposes.

The various drug delivery systems disclosed herein are ideally suited for use with, and preferably incorporates various microfabricated pump and valve systems as disclosed in U.S. Patent Applications Ser. Nos. 60/186,856, filed Mar. 3, 2000; 60/147,199, filed Aug. 3, 1999; 60/141,503, filed Jun. 28, 1999 and Ser. No. 09/605,520, filed Jun. 27, 2000.

Part I—an Implantable Drug Delivery Device

Figure 1:
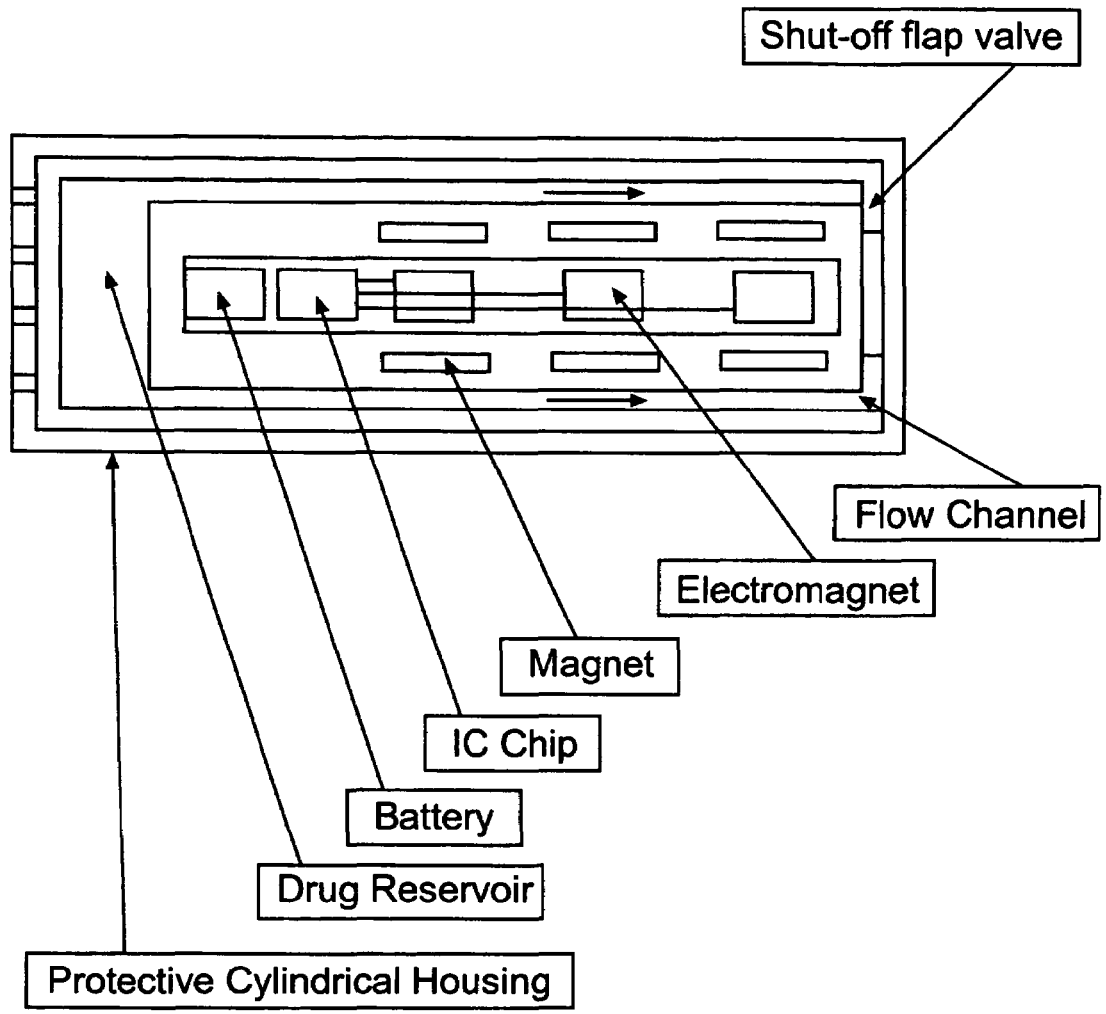

An exemplary embodiment of an implantable drug delivery device is shown in FIG. 1. It consists of a implant, (which may preferably be cylindrical in shape) which preferably also comprises the following features.
1. A protective outer housing that prevents any deformation of the structure during implantation and in-use life.
2. A pre-filled drug reservoir that opens into one or more delivery micro flow channels
3. A battery operated pump module with flow control logic.

The protective housing can be made from any biologically inert material that will prevent buckling of the drug reservoir during implantation and while the delivery system is in use. The delivery end of this housing has openings (which may in a exemplary aspect be circular or rectangular) to allow the micro flow channels (which are connected to the drug reservoir) to discharge the drug into the patient's body. The circular area of the protective housing may be solid. The drug-reservoir end of the housing preferably has one or more circular openings or an optional mesh-like structure to both protect the drug reservoir during handling, implantation, and use, and to allow the reservoir wall to collapse when drug has been depicted from it. An example of a biologically inert material is titanium.

An advantage of having a collapsible drug reservoir is that, as the drug is pumped out of the reservoir (by the present microfabricated pump/vale system), a negative pressure is not created in the drug reservoir.

The drug reservoir and micro flow channels are created as an integrated, monolithic structure using soft lithography from any of the elastomers that are compatible with a specific drug, and according to any of the systems set forth in U.S. Patent Applications Ser. Nos. 60/186,856, filed Mar. 3, 2000; 60/147,199, filed Aug. 3, 1999; 60/141,503, filed Jun. 28, 1999 and Attorney Docket No. 20174-00230, filed Jun. 27, 2000.

The delivery end of the micro channels (through which the drug is pumped from the drug reservoir to the surface of the device) may be terminated with any suitable valve structure, for example a duck bill narrow diameter valve or a flap valve. These valves will normally remain closed and will open under the fluid pressure of the drug during expulsion from the micro flow channels. The present integrated, monolithic structure also houses several micro magnets that are located alongside of membranes that serve as shut off valves for the micro flow channels.

The battery operated pump module with flow control logic consists of a cylindrical structure that includes a battery, a programmable IC chip, and several electromagnets. The pump module is hermetically sealed and is assembled with the drug reservoir prior to encapsulation within the protective housing. The pumping dynamics will determine the flow rate within each micro flow channel and the total delivery rate is determined by the number of micro flow channels.

Depending on the program logic, the implantable drug delivery system can provide controlled release, pulsatile delivery, or programmable delivery (such as delivery only at certain times of day, or only on certain days). The size of the drug reservoir will determine the total amount of drug delivered and the duration of such delivery. In a preferred aspect of the present invention, as the drug is depleted from the reservoir, one wall of the reservoir collapses due to the vacuum that is created and takes up the space formerly occupied by the expelled amount of drug, in a manner similar to a bag of IV solution.

In optional aspects of the invention, the exit of the micro channels could also be terminated with a micro bore tubing which extends from the device, acting as a catheter for delivery to a site that may be hard or undesirable to access with the implantable drug delivery system (ie: a site where it is difficult to position the implantable drug delivery system).

The implantable drug delivery system described above could also optionally be positioned external to the body and connected by way of a micro bore catheter to deliver the drug to specific site within the body.

Figure 3:
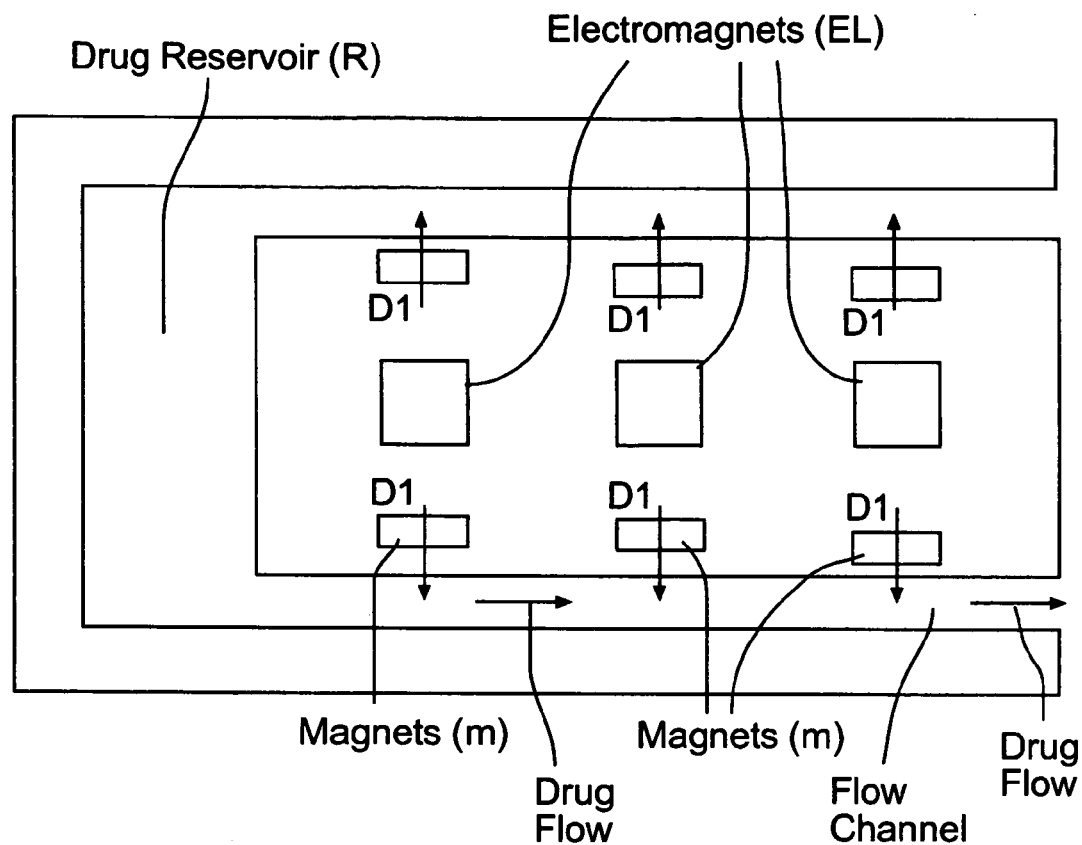
Figure 4:
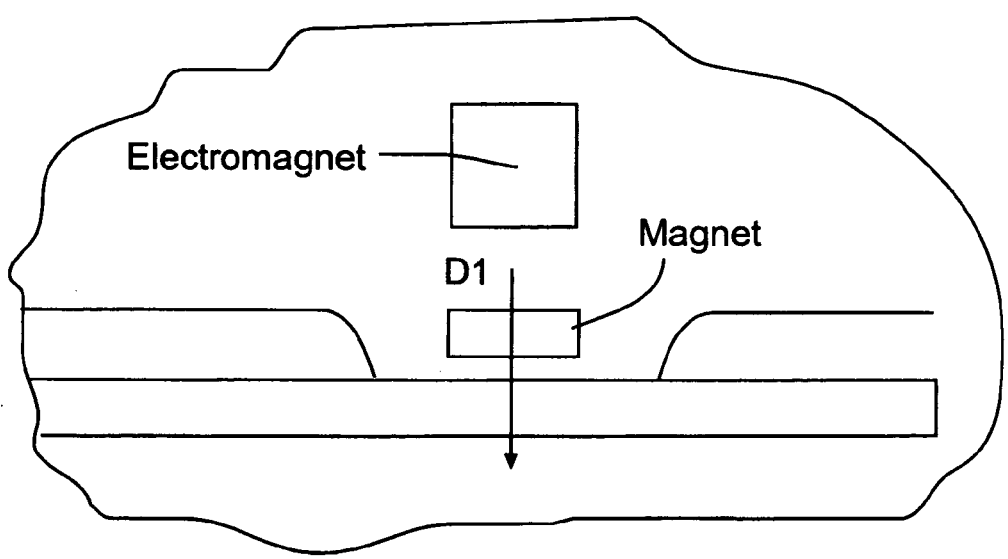
Figure 5:
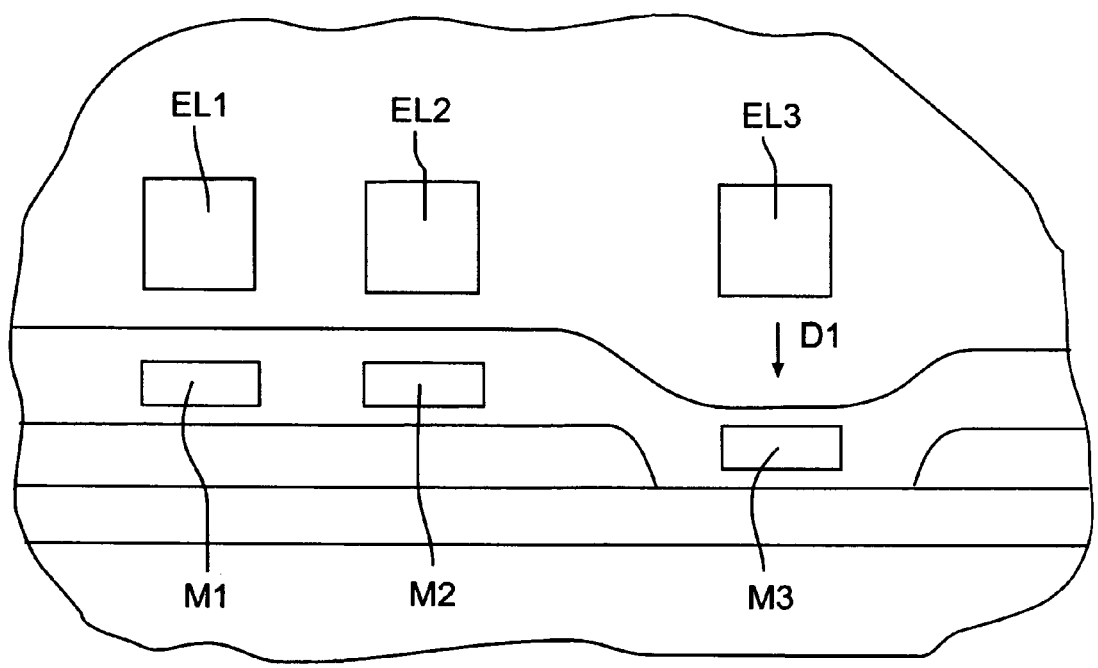

FIGS. 3, 4 and 5 illustrate an exemplary system of operation of the present device. As seen in FIG. 3, (and the breakaway close-up view of FIG. 4) a plurality of electromagnets EL1, EL2 and EL3 are provided. When electromagnets EL1, EL2 and EL3 are energized (under control of the IC Circuit of FIG. 1 and with power from the battery of FIG. 1) magnets M1, M2 and M3 move in radial directions D1, as shown.

In a preferred aspect of the present invention, the electromagnets EL1, EL2 and EL3 are activated in sequence (FIG. 5 shows only EL3 activated, pushing M3 in direction D1, thereby pinching off flow through the flow channel passing from the drug reservoir into the patient's body such that the drug is peristaltically pumped through the flow channel into the patient's body.

Figure 6:
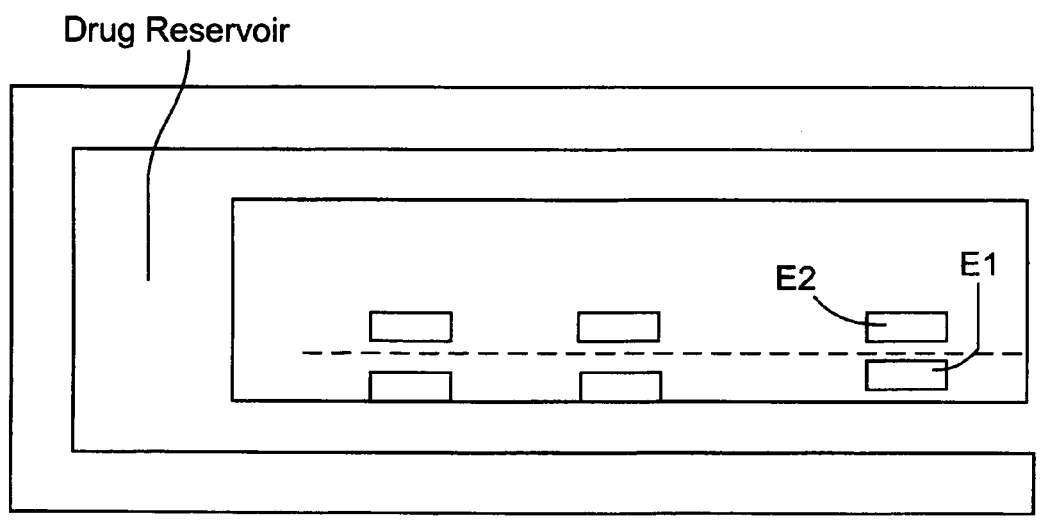
Figure 7:
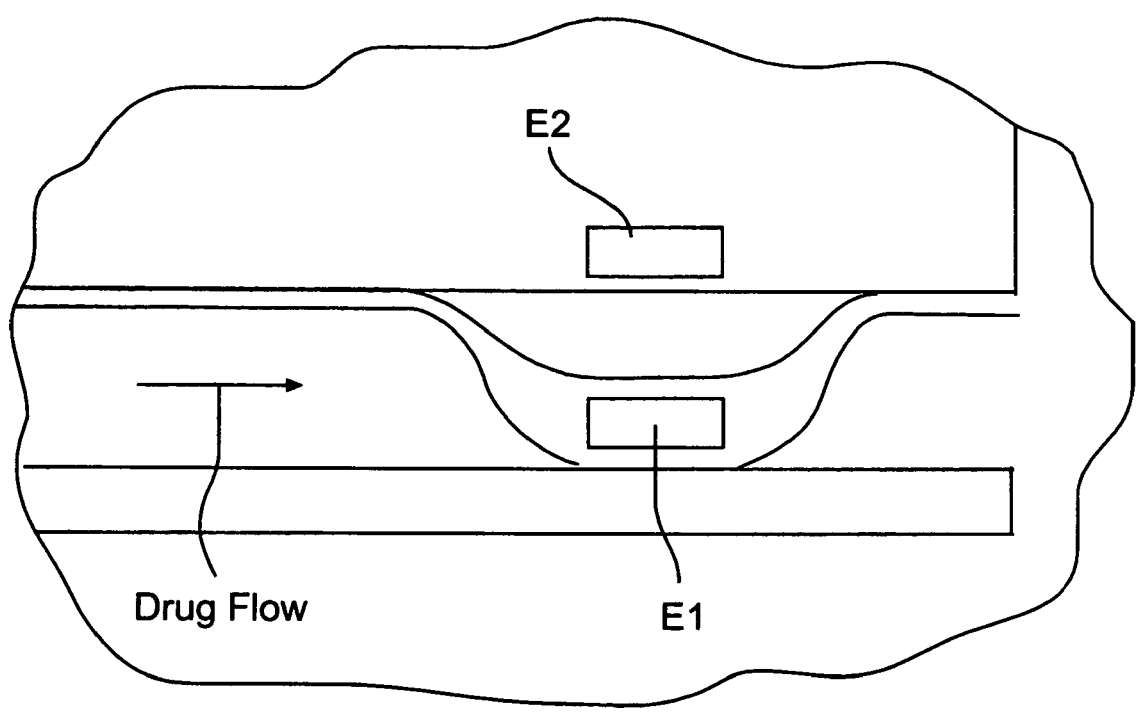

It is to be understood that peristaltic pumping can be achieved by magnetic actuation (as illustrated in FIGS. 1, 3, 4 and 5, and also by pneumatic actuation, as described in U.S. Patent Applications Ser. Nos. 60/186,856, filed Mar. 3, 2000, 60/147,199, filed Aug. 3, 1999; 60/141,503, filed Jun. 28, 1999 and filed Jun. 27, 2000. In an example of pneumatic actuation, at least 3 control channels (which arc disposed adjacent the flow channel, crossing over the flow channel such that an elastomeric membrane disposed therebetween is deflected into the flow channel when the control channel(s) are pressurized) can also be used to peristaltically pump fluid through the flow channel. In addition to pneumatic and magnetic actuation, electrostatic actuation is also contemplated. For example, as shown in FIG. 6 (and the break away close up of FIG. 7), opposite electroded surfaces E1 and E2 may be energized such that they repel one another, and thereby move apart from one another, causing E1 to deflect into the flow channel.

In the various aspects of the invention in which magnets M or electroded surfaces E are used for peristaltic pumping, the present structure preferably comprises a multi-layer elastomeric block, with a portion of the elastomeric block comprising a membrane which either separates the control channel from the flow channel, or separates a portion of the elastomeric block in which a magnet M or an electroded surface E, thereby permitting movement of the portion of the block comprising magnet M or an electroded surface E into the flow channel.

Part II—Transdermal Delivery of Medicinal Agents

In another aspect of the invention, a monolithic microfabricated pump/valve system can be used to deliver a medicinal agent through the stratum corneum of the skin, akin to a transdermal patch. In this aspect of the present invention, the present system is placed at an external location on the patient's body and the system delivers drugs directly to the surface of the patient. The drug(s) then diffuse into the patient's body through the stratum corneum. Various optional techniques are available to enhance the transport rate through the skin barrier. These include, for example, the use of permeation enhancers and/or the disruption of the stratum corneum by mechanical or other means.

The present transdermal delivery system can also be used to meter precise amounts of a drug for delivery at a predetermined rate and/or delivery profile. This rate of delivery could be modified as desired. An exemplary embodiment of such a device would he similar to the implantable device shown in FIG. 1, however, the aspect ratio could be such that the diameter of the cylinder is instead much larger than the height of the device such that the system can be easily worn like a transdermal patch on the skin.

Part III—Transdermal Body Fluid Sampling and Diagnosis

Figure 2:
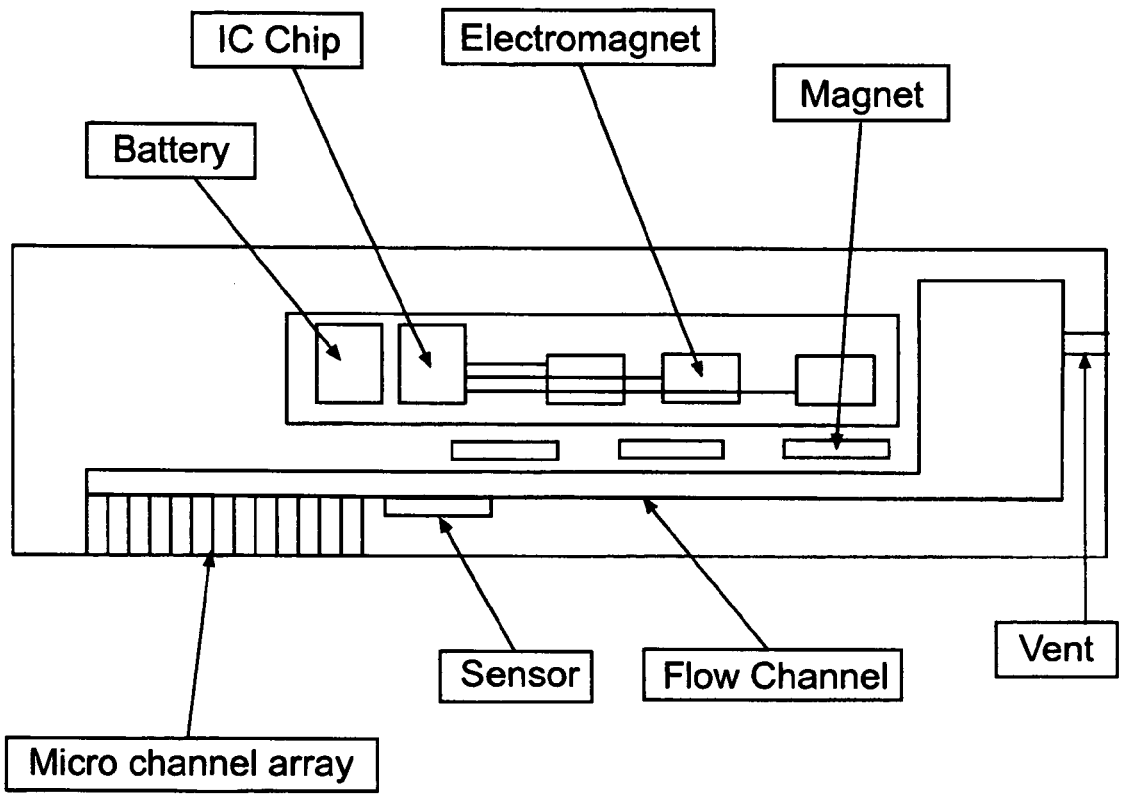

FIG. 2 illustrates a transdermal body fluid sampling device in accordance with the present invention. One exemplary use of such a device would be to measure glucose in interstitial body fluids to determine when and if to deliver insulin in diabetes management. In one embodiment of such a device, a thin gel layer is located underneath an array of micro channels that lead to a single flow channel (which is in turn connected to the drug reservoir). Within this larger channel is a sensor that measures the amount of glucose in interstitial body fluid.

Upon actuation, the larger flow channel will create a vacuum that will assist the flow of IBF into the array of micro channels and then allow it to flow past a sensor located inside the larger channel. The sensor will measure the amount of glucose and display the results.

The present invention also comprises systems which combine a sampling system with a drug delivery system (and link them to provide sensing-loop controlled drug delivery). In the case of insulin delivery, for example, this would be a tremendous benefit in diabetes management.

Part IV—Exemplary Drugs

In accordance with the present invention, any suitable drug may be dispensed. This list of drugs includes, but is not limited to the following:

Therapeutic Drugs:
Central Nervous System
Cardiovascular
Inner Ear
Oncology
Ocular
Tissue Engineering
Neurological
Inner Cranial
Rheumatoid Arthritis
Parkinson's Diseases
Contraception
Anti-Epileptics
Anemia
Diabetes
Multiple Sclerosis
Schizophrenia
AIDS Infections Other:
Chemical Make-up
Small Molecule
Protein (large molecule)

The invention claimed is:

1. An implantable drug delivery system, comprising:
a housing;
a collapsible reservoir disposed in the housing;
a microfabricated flow channel connected at one end to the collapsible reservoir, and further opening at an external surface of the housing;
at least one magnet disposed within the housing adjacent a membrane defining the flow channel, the magnet being movable in response to a magnetic force to deflect the membrane into the flow channel for inhibiting drug flow from the collapsible reservoir to the external surface of the housing, and for pumping drug flow from the collapsible reservoir to the external surface of the housing,
wherein the at least one magnetic comprises:
three magnets disposed adjacent the membrane, the three magnets being capable of sequential activation, each collapsing the flow channel in a region adjacent thereto, thereby peristaltically pumping the drug through the flow channel.

2. The implantable drug delivery system recited in claim 1, further comprising an electromagnet disposed within the housing to provide the magnetic force.

3. The implantable drug delivery system recited in claim 2, further comprising a power source disposed within the housing and coupled with the electromagnet.

4. The implantable drug delivery system recited in claim 1, wherein a wall of the collapsible reservoir is adapted to collapse in response to vacuum that is created as drug is depleted from the reservoir and to take up space formely occupied by an expelled amount of drug.

5. The implantable drug delivery system recited in claim 1, further comprising an electromagnet disposed within the housing to provide the magnetic force.

6. The implantable drug delivery system recited in claim 5, further comprising a power source disposed within the housing and coupled with the electromagnet.

7. The implantable drug delivery system recited in claim 1, wherein a wall of the collapsible reservoir is adapted to collapse in response to vacuum that is created as drug is depleted from the reservoir and to take up space formely occupied by an expelled amount of drug.

* * * * *